United States Patent [19]

Skotnicki

[11] Patent Number: 4,826,971

[45] Date of Patent: May 2, 1989

[54] 1-DIARYLMETHYL-1,2-DIOZETIDIN-3-ONE DERIVATIVES

[75] Inventor: Jerauld S. Skotnicki, Chadds Ford, Pa.

[73] Assignee: American Home Products Corporation, New York, N.Y.

[21] Appl. No.: 625,383

[22] Filed: Jun. 28, 1984

[51] Int. Cl.⁴ ............... C07D 229/00; A61K 31/395; C07B 46/03
[52] U.S. Cl. .................................................. 540/202
[58] Field of Search ................. 260/239 AR, 540, 202

[56] References Cited

PUBLICATIONS

Taylor et al., J.A.C.S., 103, 7743, (1981).
Taylor et al., Chem. Abs., 101, 7125g, (1984).
The Merck Manual, 14th Edition, (1982), pp. 149–150, 153.
Taylor et al., JACS, 103, 7659, (1981).
Taylor et al., J. Organic Chem. 48, 4567, (1983).
Taylor et al., JACS, 90, 5272, (1968).

Primary Examiner—Mark L. Berch
Attorney, Agent, or Firm—George Tarnowski

[57] ABSTRACT

There are disclosed compounds having the formula

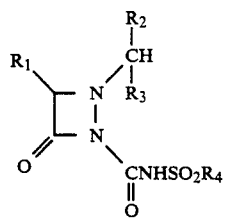

wherein
 $R_1$ is hydrogen, alkyl of 1–10 carbon atoms, phenyl or phenyl substituted with halo, lower alkyl, lower alkoxy, nitro, cyano or lower alkoxycarbonyl;
 $R_2$ and $R_3$ are phenyl or phenyl mono- or di- substituted with halo, lower alkyl, lower alkoxy, nitro, cyano, diloweralkylamino or lower alkoxycarbonyl and $R_2$ and $R_3$ may be the same or different; and
 $R_4$ is alkyl of 1–10 carbon atoms, phenyl or phenyl mono- or di- substituted with halo, lower alkyl, lower alkoxy, cyano, nitro or lower alkoxycarbonyl;
and their use as antifungal agents.

6 Claims, No Drawings

1-DIARYLMETHYL-1,2-DIOZETIDIN-3-ONE DERIVATIVES

The invention relates to 1-diarylmethyl-1,2-diazetidin-3-one derivatives and their use as antifungal agents.

The invention is directed to compounds having the formula

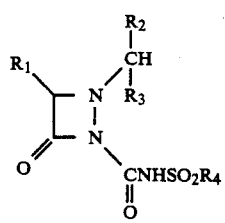

wherein
- $R_1$ is hydrogen, alkyl of 1–10 carbon atoms, phenyl or phenyl substituted with halo, lower alkyl, lower alkoxy, nitro, cyano or lower alkoxycarbonyl;
- $R_2$ and $R_3$ are phenyl or phenyl mono- or di-substituted with halo, lower alkyl, lower alkoxy, nitro, cyano, diloweralkylamino or lower alkoxycarbonyl and $R_2$ and $R_3$ may be the same or different; and
- $R_4$ is alkyl of 1–10 carbon atoms, phenyl or phenyl mono- or di-substituted with halo, lower alkyl, lower alkoxy, cyano, nitro or lower alkoxycarbonyl.

The term "halo" refers to fluoro, chloro and bromo. The terms "lower alkyl" and "lower alkoxy" refer to straight or branched chain moieties having 1–6 carbon atoms. Alkyl groups having 1–10 carbon atoms in the carbon chain may likewise be straight or branched.

The preferred compounds are those wherein $R_1$ is hydrogen, methyl or phenyl, $R_2$ are both phenyl and $R_4$ is p-chloro- or p-methylphenyl.

The compounds of the invention are prepared in the following manner:

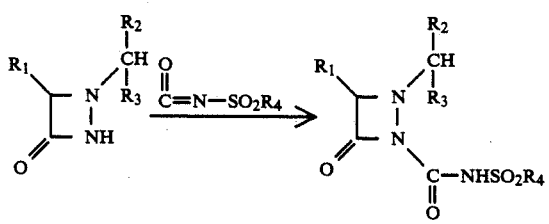

The reaction is carried out in an inert organic solvent, for example methylene chloride, at ambient temperature and under a nitrogen atmosphere. The desired products are recovered using conventional procedures, for example, solvent removal under reduced pressure followed by solvent extraction of the resulting residue.

The starting 1,2-diazetidin-3-ones used in the above reaction scheme are prepared according to the method of Taylor et al., Journal of the American Chemical Society, 103, 7743 (1981). In this method an appropriate α-haloacyl ketone hydrazone is treated with a strong non-nucleophilic base, such as sodium hydride or potassium t-butoxide in an inert anhydrous solvent, such as tetrahydrofuran or benzene, to yield a 1-(diphenylmethylene)-3-oxo-1,2-diazetidinium ylide:

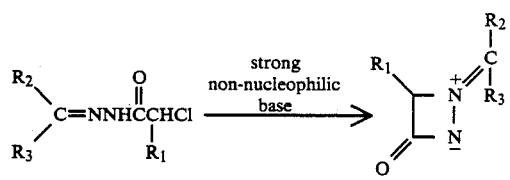

The product of the above reaction is quite stable and is readily recovered, if desired, for conversion to the 1-(diphenylmethyl)diazetidin-3-ones as follows:

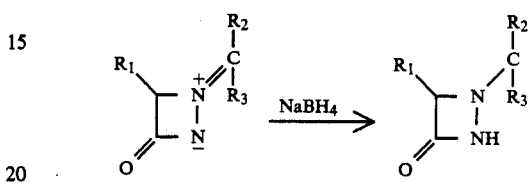

The reduction, using sodium borohydride, selectively reduces the iminium bond, giving the desired intermediates which can be readily recovered by conventional techniques. These intermediates can then be used for preparation of the compounds of the invention by the method outlined, supra.

The α-haloacyl ketone hydrazones, which are used as the starting materials for preparing the intermediates discussed above are either commercially available or can be prepared by standard preparative chemical methods, such as for example that disclosed by Taylor et al., JACS, 103, 7748 (1981).

The compounds of the invention are useful agents in combatting fungi. For example, the compounds have been found active against a variety of pathogenic fungi, such as *Candida albicans, Cryptococcus neoformans, Trichophyton mentagrophytes, Histoplasma capsulatum* and *Blastomyces dermatitidis*. Because of their antifungal activity, the compounds of the invention are useful in the destruction and prevention of the growth of fungi and as such can be effectively used in the treatment of subjects suffering from fungal infection.

Because of their antifungal properties, the compounds of the invention can be formulated into therapeutically valuable compositions comprising compounds of the invention and pharmacologically acceptable carriers. The latter term contemplates usual and customary substances employed to formulate solid, oral unit dosages for pharmacological purposes. The term also includes those substances employed to formulate either in unit dose or multidose form, oral and injectable suspensions and solutions, either directly or for reconstitution before administration.

To formulate dosages for administration according to this invention the compounds of the invention can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases, the proportion of active ingredients in said compositions both solid and liquid will be at least sufficient to impart antifungal activity thereto on oral administration.

The compounds may also be injected parenterally, in which case they are used in the form of a sterile solution containing other solutes, for example, enough saline or glucose to make the solution isotonic. The compounds may also be used topically and for this purpose they may be formulated in the form of dusting powders, solutions, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects.

The antifungal activity of the compounds of the invention may be demonstrated by a standard pharmacological procedure which is described fully following the below presented examples directed to the preparation of the compounds useful in the invention.

EXAMPLE 1

Preparation of 1-(Diphenylmethyl)-1,2-diazetidin-3-one Intermediates

A. 1-(Diphenylmethyl)-1,2-diazetidin-3-one 1. 1-(Diphenylmethylene)-3-oxo-1,2-diazetidinium ylide To a solution of 0.01 mol of benzophenone α-chloroacetylhydrazone in 30 mL of dry benzene or tetrahydrofuran is added 0.01 mol of 60% sodium hydride (in mineral oil) in small portions. After the addition is complete, the solution is stirred at room temperature for 24 hours. Following the addition of 20 mL of 50% ammonium chloride solution, the organic layer is separated, dried over magnesium sulfate, and evaporated under reduced pressure. m.p. 175°–181° C.

Analysis for: $C_{15}H_2N_2O$, Calculated: C, 76.25; H, 5.12; N, 11.86, Found: C, 75.00; H, 5.33; N, 11.29.

2. 1-(Diphenylmethyl)-1,2-diazetidin-3-one

To a solution or slurry of 0.01 mol of the ylide of 1) above in 25 mL of methanol at 0° C. is added, in small portions, 0.01 mol of sodium borohydride. After addition is complete, the reaction mixture is stirred for 1 hour and poured over 10 g of ice; the reduction product is recovered. m.p. 160°–163° C.

Analysis for: $C_{15}H_{14}N_2O$, Calculated: C, 75.60; H, 5.93; N, 11.76, Found: C, 75.08; H, 6.18; N, 11.38.

B. 1-(Diphenylmethyl)-4-methyl-1,2-diazetidin-3-one

Following the above procedures, there are obtained:
1. 1-(Diphenylmethylene)-4-methyl-3-oxo-1,2-diazetidinium ylide m.p. 126°–131° C.

Analysis for: $C_{16}H_{14}N_2O$, Calculated: C, 76.77; H, 5.63; N, 11.20, Found: C, 75.76; H, 5.84; N, 11.26.

2. 1-(Diphenylmethyl)-4-methyl-1,2-diazetidin-3-one m.p. 156°–158° C.

Analysis for: $C_{16}H_{16}N_2O$, Calculated: C, 76.16; H, 6.39; N, 11.11, Found: C, 75.17; H, 6.24; N, 11.10.

C. 1-(Diphenylmethyl)-4-phenyl-1,2-diazetidin-3-one

Following the above procedures there are obtained:
1. 1-(Diphenylmethylene)-3-oxo-4-phenyl-1,2-diazetidinium ylide m.p. 193°–194° C.

Analysis for: $C_{21}H_{16}N_2O$, Calculated: C, 80.74; H, 5.16; N, 8.97, Found: C, 80.56; H, 5.16; N, 8.77.

2. 1-(Diphenylmethyl)-4-phenyl-1,2-diazetidin-3-one m.p. 155°–157° C.

Analysis for: $C_{21}H_{18}N_2O$, Calculated: C, 80.23; H, 5.77; N, 8.91, Found: C, 79.79; H, 5.83; N, 8.89.

EXAMPLE 2

1-(Diphenylmethyl)-N-[(4-methylphenyl)sulfonyl]-3-oxo-1,2-diazetidine-2-carboxamide To a solution of 1 g of 1-(diphenylmethyl)-1,2-diazetidin-3-one (prepared according to Example 1A.) in 20 mL of methylene chloride, at ambient temperature and under a nitrogen atmosphere, there is added in one portion a solution of one equivalent of p-toluenesulfonylisocyanate in methylene chloride. The reaction mixture is stirred at ambient temperature for 24–72 hours. The solvent is removed under reduced pressure followed by trituration of the residue with ethyl ether to yield 970 mg (53%) of the title compound having a melting point of 115°–123° C.

IR 1810, 1740, 1430, 1350 and 1170 cm$^{-1}$;

$^1$H NMR (CDCl$_3$) 8.0–7.2 (m, 15H), 5.05 (s, 1H), 4.75–3.8 (m, 2H) and 2.47 (s, 3H).

Analysis for: $C_{23}H_{21}N_3O_4S$, Calculated: C, 63.43; H, 4.86; N, 9.65; Found: C, 61.79; H, 5.07; N, 9.46.

EXAMPLE 3

1-(Diphenylmethyl)-4-methyl-N-[(4-methylphenyl)sulfonyl]-3-oxo-1,2-diazetidine-2-carboxamide Following the procedure of Example 2 and using 1-(diphenylmethyl)-4-methyl-1,2-diazetidin-3-one (prepared according to Example 1B.) and p-toluenesulfonylisocyanate there is obtained 1.15 g (64%) of the title compound having a melting point of 155°–159° C.

IR 3300, 1810, 1740, 1440, 1360, and 1170 cm$^{-1}$;

$^1$H NMR (CDCl$_3$) 8.35–7.15 (m, 15H), 4.9 (s, 1H), 4.1 (q, 1H), and 1.42 (d, 2H).

Analysis for: $C_{24}H_{23}N_3O_4S$, Calculated: C, 64.12; H, 5.16; N, 9.35, Found: C, 62.88; H, 5.24; N, 9.18.

EXAMPLE 4

1-(Diphenylmethyl-N-[(4-methylphenyl)sulfonyl]-3-oxo-4-phenyl-1,2-diazetidine-2-carboxamide Following the procedure of Example 2 and using 1-(diphenylmethyl)-4-phenyl-1,2-diazetidin-3-one (prepared according to Example 1C.) and p-toluenesulfonylisocyanate there is obtained 1.1 g (68%) of the title compound having a melting point of 154°–156° C.

IR 3250, 1810, 1750, 1410, 1350, and 1160 cm$^{-1}$;

$^1$H NMR (CDCl$_3$) 8.2–6.9 (m, 20H), 5.15 (s, 1H), 4.98 (s, 1H), and 2.45 (s, 3H).

Analysis for: $C_{29}H_{25}N_3O_4S$ Calculated: C, 68.08; H, 4.93; N, 8.21 Found: C, 66.09; H, 5.07; N, 7.98.

EXAMPLE 5

N-[(4-Chlorophenyl)sulfonyl]-1-(diphenylmethyl)-4-methyl-3-oxo-1,2-diazetidine-2-carboxamide Following the procedure of Example 2 and using 1-(diphenylmethyl)-4-methyl-1,2-diazetidin-3-one (prepared according to Example 1B.) and p-chlorophenylsulfonylisocyanate there is obtained 1.7 g (88%) of the title compound having a melting point of 124°–129° C.

IR 3300, 1810, 1740, 1430, 1370, and 1170 cm$^{-1}$;

$^1$H NMR (CDCl$_3$) 8.05–7.2 (m, 15H), 4.85 (s, 1.H), 4.07 (q, 1H), and 1.4 (d, 3H).

Analysis for: C$_{23}$H$_{20}$N$_3$O$_4$ClS, Calculated: C, 58.78; H, 4.29; N, 8.95, Found: C, 55.86; H, 4.24; N, 8.45.

EXAMPLE 6

N-[(4-Chlorophenyl)sulfonyl]-1-(diphenylmethyl)-3-oxo-4-phenyl-1,2-diazetidine-2-carboxamide Following the procedure of Example 2 and using 1-(diphenylmethyl)-4-phenyl-1,2-diazetidin-3-one (prepared according to Example 1C.) and p-chlorophenylsulfonylisocyanate there is obtained 890 mg (53%) of the title compound having a melting point of 162°–163° C.

IR 3220, 1800, 1750, 1430, 1340, 1230, and 1160 cm$^{-1}$;

$^1$H NMR (CDCl$_3$) 8.08–7.10 (m, 20H), 5.14 (s, 1H), and 5.0 (s, 1H).

Analysis for: C$_{28}$H$_{22}$N$_3$O$_4$ClS, Calculated: C, 63.21; H, 4.17; N, 7.90, Found: C, 62.51; H, 4.31; N, 7.82.

EXAMPLE 7

The compounds of the invention are tested to determine their antifungal activity. The assay procedure is as follows:

The compounds to be tested are solubilized or suspended in appropriate reagent and further diluted in sterile distilled water to provide a range of concentrations from 200 to 10 μg/ml. 20 lambda portions are placed on sterile dried ¼ inch paper discs and allowed to dry for 20–30 minutes. Agar plates with a 10 ml base layer are seeded with the fungi in a 4 ml seed layer and allowed to solidify. The impregnated discs are then placed on the seeded agar surface and incubated for the time required for the particular culture.

The representative fungi are:

| | |
|---|---|
| *Candida albicans* | ATCC 10231 |
| *Cryptococcus neoformans* | ATCC 14115 |
| *Histoplasma capsulatum* | ATCC 11407 - yeast phase |
| *Blatomyces dermatitidis* | ATCC 28839 - yeast phase |
| *Trichophyton mentagrophytes* | ATCC 9533 |

All are human pathogens; the first four cause serious systemic mycotic infections as well as local. The trychophyton culture is mainly a dermatophyte.

The zones of inhibition are measured and the results for the given concentration of compound are tabulated in Table 1 below.

TABLE 1

| | Zone Size, mm (Concentration, μg/ml) | | | | |
|---|---|---|---|---|---|
| Example (Compound) | *Candida Albicans* ATCC 10231 | *Cryptococcus Neoformans* ATCC 14115 | *Trichophyton Mentagrophytes* ATCC 9533 | *Histoplasma Capsulatum* Yeast Phase ATCC 11407 | *Blastomyces Dermatitidis* Yeast Phase ATCC 28839 |
| 2 | 0(200) | 10(200) | 0(200) | 0(200) | 25(200) |
| 3 | 0(200) | 11.3(200) | 0(200) | 25(200) | 27(200) |
| 4 | 0(200) | 9(200) | 0(200) | 30(100) | 25(10) |
| 5 | 9(200) | 8(200) | 9(200) | 22.3(200) | 9.3(100) |
| 6 | 0(200) | 8.7(200) | 9.7(200) | 29.3(100) | 24.7(100) |

The results show that the compounds of the invention have antifungal activity against a variety of pathogenic fungi.

What is claimed is:

1. A compound having the formula

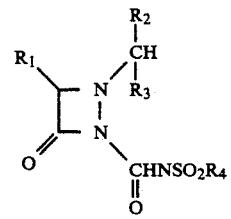

wherein

R$_1$ is hydrogen, alkyl of 1–10 carbon atoms, phenyl or phenyl substituted with halo, lower alkyl, lower alkoxy, nitro, cyano or lower alkoxycarbonyl;

R$_2$ and R$_3$ are phenyl or phenyl mono- or di-substituted with halo, lower alkyl, lower alkoxy, nitro, cyano, diloweralkylamino or lower alkoxycarbonyl and R$_2$ and R$_3$ may be the same or different; and R$_4$ is alkyl of 1–10 carbon atoms, phenyl or phenyl mono- or di-substituted with halo, lower alkyl, lower alkoxy, cyano, nitro or lower alkoxycarbonyl.

2. The compound of claim 1, having the name 1-(diphenylmethyl)-N-[(4-methylphenyl)sulfonyl]-3-oxo-1,2-diazetidine-2-carboxamide.

3. The compound of claim 1, having the name 1-(diphenylmethyl)-4-methyl-N-[4-methylphenyl)sulfonyl]-3-oxo-1,2-diazetidine-2-carboxamide.

4. The compound of claim 1, having the name 1-(diphenylmethyl)-N-[(4-methylphenyl)sulfonyl]-3-oxo-4-phenyl-1,2-diazetidine-2-carboxamide.

5. The compound of claim 1, having the name N-[(4-chlorophenyl)sulfonyl]-1-(diphenylmethyl)-4-methyl-3-oxo-1,2-diazetidine-2-carboxamide.

6. The compound of claim 1, having the name N-[(4-chlorophenyl)sulfonyl]-1-(diphenylmethyl)-3-oxo-4-phenyl-1,2-diazetidine-2-carboxamide.

* * * * *